(12) United States Patent
Naidu

(10) Patent No.: US 8,592,588 B2
(45) Date of Patent: Nov. 26, 2013

(54) PROCESS TO PREPARE CAMPTOTHECIN DERIVATIVES

(75) Inventor: Ragina Naidu, Burnaby (CA)

(73) Assignee: Chatham Biotec, Limited, Riverview, New Brunswick (CA)

( * ) Notice: Subject to any disclaimer, the term of this patent is extended or adjusted under 35 U.S.C. 154(b) by 1271 days.

(21) Appl. No.: 11/628,055

(22) PCT Filed: May 27, 2005

(86) PCT No.: PCT/US2005/018793
§ 371 (c)(1),
(2), (4) Date: May 28, 2008

(87) PCT Pub. No.: WO2005/117879
PCT Pub. Date: Dec. 15, 2005

(65) Prior Publication Data
US 2008/0280935 A1 Nov. 13, 2008

Related U.S. Application Data

(63) Continuation-in-part of application No. 10/857,170, filed on May 28, 2004, now abandoned.

(51) Int. Cl.
*C07D 491/22* (2006.01)
*C07D 401/04* (2006.01)

(52) U.S. Cl.
USPC .......................................... 546/48; 546/186

(58) Field of Classification Search
USPC .................................................. 546/48, 186
See application file for complete search history.

(56) References Cited

U.S. PATENT DOCUMENTS

| | | | |
|---|---|---|---|
| 4,473,692 A | 9/1984 | Miyasaka et al. | |
| 4,604,463 A * | 8/1986 | Miyasaka et al. | 544/125 |
| 5,112,859 A | 5/1992 | Commons et al. | |
| 5,391,571 A | 2/1995 | Mewshaw et al. | |
| 6,294,555 B1 | 9/2001 | Kato et al. | |
| 2004/0132716 A1 | 7/2004 | Rudolf et al. | |
| 2008/0051580 A1 | 2/2008 | Naidu | |

FOREIGN PATENT DOCUMENTS

| | | |
|---|---|---|
| EP | 0137145 A | 4/1985 |
| EP | 0321122 A1 | 6/1989 |
| EP | 0990661 A | 4/2000 |
| EP | 1201649 | 5/2002 |
| EP | 1791539 | 8/2009 |
| WO | 92/05785 | 4/1992 |
| WO | 92/07856 | 5/1992 |
| WO | WO2004/037811 | 5/2004 |
| WO | 2005/117881 | 12/2005 |

OTHER PUBLICATIONS

Sewada, S. et al.: Synthesis and antitumor activity of 20(S)-camptothecin derivatives. Carbamate-linked, water soluble derivatives of 7-ethyl-10-hydroxycamptothecin. Chem. Pharm. Bull., vol. 39, pp. 1446-1454, 1991.*
International Search Report and Written Opinion for PCT/US2005/019700 (mailed Nov. 17, 2005).
Bourzat, Jean-Dominique et al., "Semisynthesis of RPR 121056A, a Major Metabolite of Irinotecan (CPT-11)," *Tetrahedron Letter*, vol. 37, No. 35, pp. 6327-6330 (Aug. 1996).
He, Wei et al., "Novel Cyclic Compounds as Potent Phosphodiesterase 4 Inhibitors," *J. Med. Chem.*, vol. 41, pp. 4216-4223 (Oct. 1998).
International Search Report and Written Opinion for PCT/US2005/018793 (mailed Sep. 28, 2005).
Li, Yu-yan et al., "Improving Synthetic Method of Irinotecan," *Chinese Journal of Medicinal Chemistry*, vol. 11, No. 4, pp. 238-240 (Aug. 2001)—English translation.
Opposition Brief Filed by Opposer Against EP1791539 on May 26, 2010—all statements in the Brief are those made by the Opposer and do not reflect or represent the European Patent Office's views or opinions.
Ullmann's Encyclopedia of Industrial Chemistry, vol. 6, Wiley-VCH Verlag GmbH & Co. KGaA Weinheim, Carbamates and Carbamoyl Chlorides, pp. 207-214 (2003).

* cited by examiner

*Primary Examiner* — Charanjit Aulakh
(74) *Attorney, Agent, or Firm* — Klarquist Sparkman, LLP

(57) ABSTRACT

A process is provided for the preparation of camptothecin derivatives, such as irinotecan, in a one-pot operation.

19 Claims, 2 Drawing Sheets

EXATECAN, 5

LURTOTECAN, 6

CKD-602, 7

PROCESS TO PREPARE CAMPTOTHECIN DERIVATIVES

This is the U.S. National Stage of International Application No. PCT/US2005/018793, filed May 27, 2005, which was published in English under PCT Article 21(2), which is a Continuation-in-Part of U.S. application Ser. No. 10/857,170, filed May 28, 2004 now abandoned.

BACKGROUND OF THE INVENTION

1. Field of the Invention

The present invention relates to improved processes to prepare camptothecin derivatives, such as irinotecan, in a one-pot operation.

2. Description of the Related Art

Camptothecin 1 (shown in FIG. 1A) is a pentacyclic alkaloid that was isolated by Wall et al. in the early 1960s from the Chinese tree, *Camptotheca acuminate* (Nyssaceae). The compound raised immediate interest as a potential cancer chemotherapeutic agent due to its impressive activity against a variety of tumors. However, a shortcoming of camptothecin as an anti-cancer agent was its poor solubility in water. To overcome the solubility problem, the sodium salt was synthesized by hydrolysis of the lactone ring. The sodium salt forms an equilibrium with the ring-closed lactone form. As its sodium salt, camptothecin was moved to clinical trials and promising activity was initially observed. However severe side effects and drug-related toxicities finally led to discontinuation of the clinical program.

Stimulated by the challenging structure and its very interesting biological activity, synthetic approaches to camptothecin were developed. During semi-synthetic and total-synthetic chemistry programs, the particular importance of the lactone ring and the C20 (S)-configuration for good biological activity was recognized. In contrast, modifications in the A-ring and B-ring, particularly in the C9, C10 and C11 positions, were tolerated and led to improved analogues.

Second-generation camptothecin derivatives have been optimized for improved water solubility to facilitate intravenous drug administration. Highlights resulting from various programs at different companies and institutions are irinotecan 2 and topotecan 3, two compounds which are successfully used in clinical practice, and SN-38 4, exatecan 5, liposomal lurtotecan 6 (OSI-211) and CKD-602 7, which are in advanced stages of clinical development. The chemical structures of these compounds are shown in FIGS. 1A and 1B.

SN-38 is a camptothecin derivative that contains a hydroxyl group at the C10 position and an ethyl group at the C7 position. Irinotecan is a camptothecin derivative (it may also be viewed as a derivative of SN-38) that contains a sidechain at the C10 position and an ethyl group at the C7 position. Irinotecan was discovered at Yakult Honsha and was first approved in Japan in 1994 (Camptotesin®) for lung, cervical and ovarian cancer. Today it is marketed in the U.S. by Pharmacia (Camptosar®) and by Aventis in Europe (Campto®). Irinotecan is a prodrug which is cleaved in vivo by carboxylic esterases, particularly by hCE-2, to release the active metabolite SN-38.

The synthesis of irinotecan has been described in the chemical literature and in patents. A common approach to the synthesis of irinotecan is to form SN-38 and then add a sidechain to the C10 position of SN-38, to thereby form irinotecan. U.S. Pat. No. 4,604,463 is one example of a patent that describes this approach, wherein either an activated form of the sidechain is separately formed and then reacted with SN-38, or the C10 hydroxyl group is activated and then in a separate reaction the sidechain is added.

Although there have been advances in the field, there remains a need for improved methods to form irinotecan from SN-38. The present invention addresses this need and provides further related advantages.

BRIEF SUMMARY OF THE INVENTION

In brief, the present invention is related to improved processes to prepare camptothecin derivatives, such as irinotecan, in a one-pot operation.

In one embodiment, a process for adding a sidechain to a starting material is provided comprising reacting together: (i) a compound of formula I:

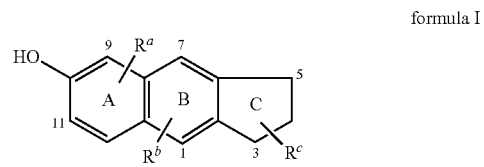

formula I wherein each of the ring atoms may be carbon, or any one, two or three of the ring atoms may be nitrogen, and $R^a$, $R^b$ and $R^c$ are the same or different and independently represent one or more optional non-hydrogen substituents on each of rings A, B and C; (ii) an amine of formula $R^1R^2NH$ wherein $R^1$ and $R^2$ are the same or different and independently represent organic groups; and (iii) phosgene or a reactive equivalent thereof, to provide a solution comprising a compound of formula III:

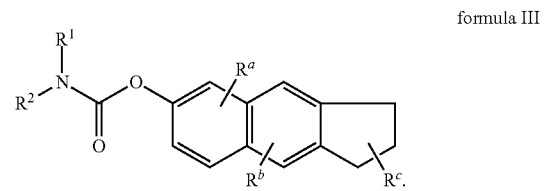

formula III

In a further embodiment of the foregoing, the phosgene or reactive equivalent thereof and the amine of formula $R^1R^2NH$ are combined to provide an intermediate solution, and the compound of formula I is added to the intermediate solution. In yet a further embodiment, the process further comprises adding pyridine or a tertiary amine to the intermediate solution along with the compound of formula I.

In another further embodiment, the process further comprises a step wherein the solution comprising a compound of formula III is filtered and then freed from solvent to provide a residue. In more specific embodiments, the residue is purified by column chromatography, filtration, precipitation or crystallization.

In a more specific embodiment of the foregoing, the compound of formula I is SN-38, the amine of formula $R^1R^2NH$ is piperidinopiperidine, and the compound of formula III is irinotecan, and the process is a one-pot operation. In particular, the phosgene or reactive equivalent thereof is phosgene trihydrate, and the phosgene trihydrate and piperidinopiperidine are combined in a solvent and allowed to react together to form an intermediate solution, and the SN-38 and an organic base are added to the intermediate solution to form the solution comprising irinotecan.

In further embodiments of the foregoing, the phosgene trihydrate is dissolved in a chlorinated solvent and then cooled to a temperature in the range of −40° C. to 25° C. followed by addition of piperidinopiperidine to the cooled solution. More particularly, the phosgene trihydrate is cooled to a temperature in the range of −10° C. to 0° C.

In yet further embodiments, (1) subsequent to the addition of piperidinopiperidine, N,N-diisopropylethylamine (Hünig's base) or triethylamine or an equivalent base is added to the cooled solution and/or (2) the process further comprises adding a catalyst to the intermediate solution along with the SN-38 and the organic base.

In a second embodiment, the present invention provides a composition comprising a solvent and the reaction product of: (i) a compound of formula I:

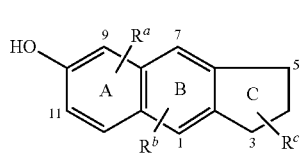

formula I wherein each of the ring atoms may be carbon, or any one, two or three of the ring atoms may be nitrogen, and $R^a$, $R^b$ and $R^c$ are the same or different and independently represent one or more optional non-hydrogen substituents on each of rings A, B and C, (ii) an amine of formula $R^1R^2NH$ wherein $R^1$ and $R^2$ are the same or different and independently represent organic groups, and (iii) phosgene or a reactive equivalent thereof.

These and other aspects of the invention will be apparent upon reference to the attached figures and following detailed description.

DETAILED DESCRIPTION OF THE INVENTION

I. Definitions

Figure 1A:
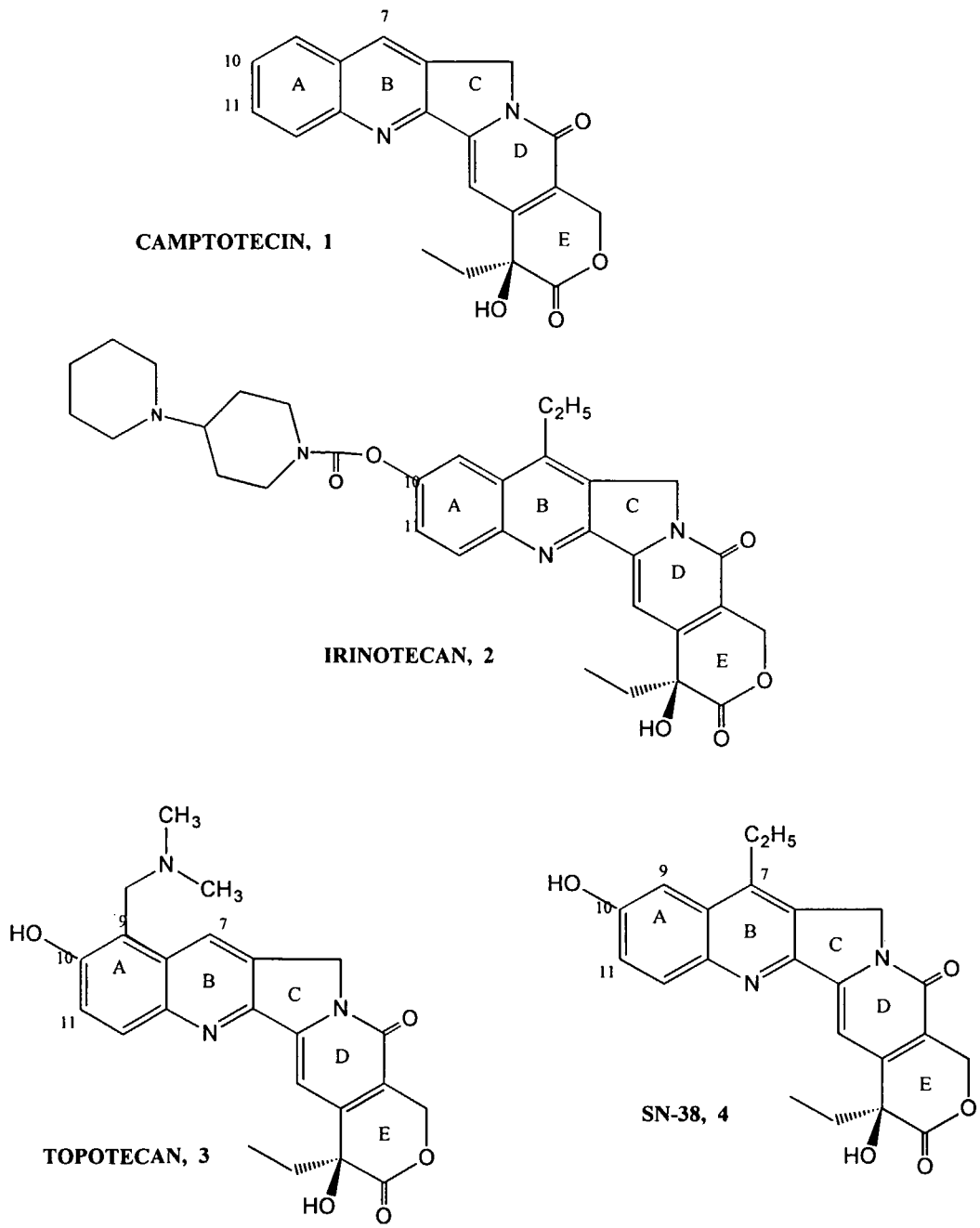
FIGS. 1A and 1B show the chemical structures of camptothecin 1 and various analogs and derivatives of camptothecin, specifically, irinotecan 2, topotecan 3, SN-38 4, exatecan 5, lurtotecan 6 and CKD-602 7.
Figure 1B:
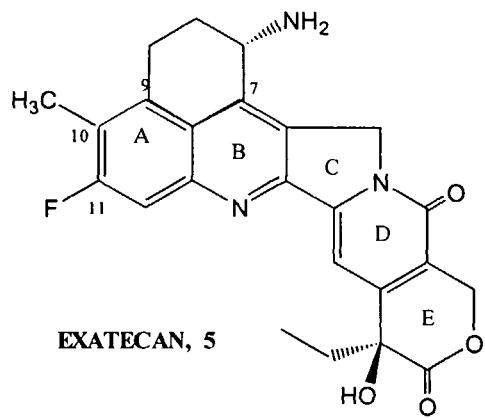
Figure 1B:
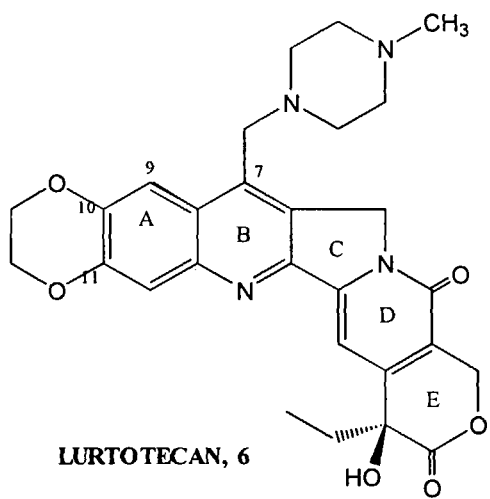
Figure 1B:
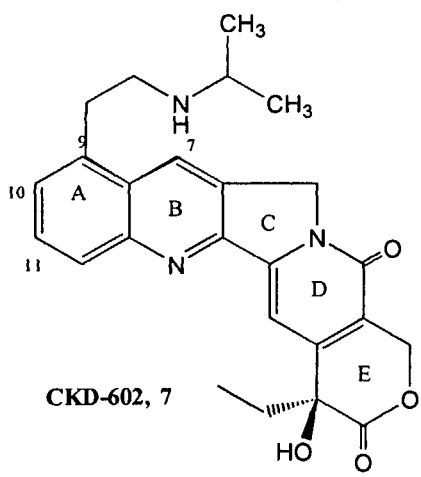

As used herein, the following terms have the following meanings.

"Alkyl" refers to a hydrocarbon structure having from 1 to 14 carbon atoms, wherein the carbons are arranged in a linear, branched, or cyclic manner, including combinations thereof. Lower alkyl refers to alkyl groups of from 1 to 6 carbon atoms. Examples of lower alkyl groups include methyl, ethyl, propyl, isopropyl, butyl, s- and t-butyl and the like. "Cycloalkyl" is a subset of alkyl and includes cyclic hydrocarbon groups of from 3 to 14 carbon atoms. Examples of cycloalkyl groups include cyclopropyl, cyclobutyl, cyclopentyl, norbornyl, adamantyl and the like. When an alkyl residue having a specific number of carbons is named, all geometric isomers having that number of carbons are intended to be encompassed; thus, for example, "butyl" is meant to include n-butyl, sec-butyl, isobutyl and t-butyl; propyl includes n-propyl and isopropyl.

"Alkenyl" refers to an alkyl group having at least one site of unsaturation, i.e., at least one double bond.

"Alkynyl" refers to an alkyl group having at least one triple bond between adjacent carbon atoms.

"Alkoxy" and "alkoxyl" both refer to moieties of the formula —O-alkyl. Examples include methoxy, ethoxy, propoxy, isopropoxy, cyclopropyloxy, cyclohexyloxy and the like. Lower-alkoxy refers to groups containing one to six carbons. The analogous term "aryloxy" refers to moieties of the formula —O-aryl.

"Alkanediyl" means a divalent alkyl from which two hydrogen atoms are taken from the same, or different, carbon atoms, such as —CH$_2$—, —CH$_2$CH$_2$—, —CH$_2$CH$_2$CH$_2$—, —CH(CH$_3$)CH$_2$—, and the like.

"Acyl" refers to moieties of the formula —C(=O)-alkyl. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"Aryl" refers to an aromatic carbocyclic moiety such as phenyl or naphthyl.

"Heteroalkyl" is a monovalent, saturated or unsaturated, straight or branched, chain containing carbon and at least one heteroatom. The heteroalkyl group may, in various embodiments, have one heteroatom, or 1-2 heteroatoms, or 1-3 heteroatoms, or 1-4 heteroatoms. Heteroalkyl chains may contain from 1 to 14 (i.e., 1-14) member atoms (carbon and heteroatoms) in the chain, and in various embodiments contain 1-12, or 1-6, or 1-4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds.

"Heteroaryl" refers to a 5- or 6-membered heteroaromatic ring containing 1-3 heteroatoms selected from O, N, or S; a bicyclic 9- or 10-membered heteroaromatic ring system containing 0-3 heteroatoms selected from O, N, or S; or a tricyclic 13- or 14-membered heteroaromatic ring system containing 0-3 heteroatoms selected from O, N, or S. Exemplary aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "substituted" as used herein means any of the above groups (e.g., alkyl, alkoxy, acyl, aryl, heteroalkyl, heteroaryl and heterocycle) wherein at least one hydrogen atom is replaced with a substituent. In the case of an oxo substituent ("=O") two hydrogen atoms are replaced. Substituents include halogen, hydroxy, oxo, alkyl, substituted alkyl, aryl, substituted aryl, heteroalkyl, substituted heteroalkyl, heteroaryl, substituted heteroaryl, heterocycle, substituted heterocycle, $-NR_aR_b$, $-NR_aC(=O)R_b$, $-NR_cC(=O)NR_aR_b$, $-NR_aC(=O)OR_b$, $-NR_aSO_2R_b$, $-OR_a$, $-C(=O)R_a$, $-C(=O)OR_a$, $-C(=O)NR_aR_b$, $-OC(=O)R_a$, $-(=O)OR_a$, $-OC(=O)NR_aR_b$, $-NR_aSO_2R_b$, or a radical of the formula $-Y-Z-R_a$ where Y is alkanediyl, substituted alkanediyl or a direct bond, Z is $-O-$, $-S-$, $-S(=O)-$, $-S(=O)_2-$, $-N(R_b)-$, $-C(=O)-$, $-C(=O)O-$, $-OC(=O)-$, $-N(R_b)C(=O)-$, $-C(=O)N(R_b)-$ or a direct bond, wherein $R_a$, $R_b$ and $R_c$ are the same or different and independently hydrogen, amino, alkyl, substituted alkyl (including halogenated alkyl), aryl, substituted aryl, heteroalkyl, substituted heteroalkyl, heteroaryl, substituted heteroaryl, heterocycle, or substituted heterocycle, or wherein $R_a$ and $R_b$ taken together with the nitrogen atom to which they are attached form a heterocycle or substituted heterocycle.

"Formyl" refers to the moiety $-C(=O)H$.

"Halogen" refers to fluoro, chloro, bromo or iodo.

II. Overview of the Invention

As noted above the present invention provides synthetic methods and compounds produced by, or using, the synthetic methods. The compounds are useful as synthetic intermediates in the preparation of derivatives and analogs of irinotecan, where the synthetic intermediates may also have desirable biological activity.

In one aspect, the present invention provides a process for adding a sidechain to a starting material, comprising reacting together:
(i) a compound of formula I:

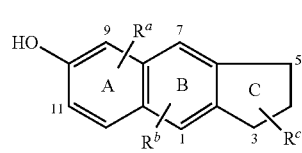

formula I wherein each of the ring atoms may be carbon, as shown, or any one, two or three of the ring atoms may be nitrogen, and $R^a$, $R^b$ and $R^c$ are the same or different and independently represent one or more optional non-hydrogen substituents on each of rings A, B and C, respectively,
(ii) an amine of formula $R^1R^2NH$ wherein $R^1$ and $R^2$ are the same or different and independently represent organic groups, and
(iii) phosgene or a reactive equivalent thereof,
to provide a compound of formula III:

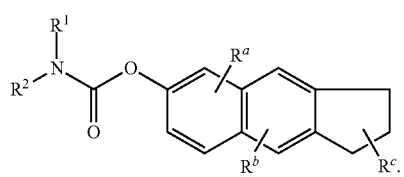

formula III

Each of the three reactants, namely, (i) a compound of formula I:

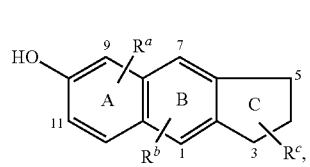

formula I (ii) an amine of formula $R^1R^2NH$, and (iii) phosgene or a reactive equivalent thereof, will now be described.

Compound of Formula I

In the structure provided above for compounds of formula I, each of the ring atoms is shown as carbon. However, this depiction is for purposes of illustration only, and is intended to encompass compounds which, in addition to being carbocyclic may have, with one exception, any one, two or three of the ring atoms replaced with nitrogen. The one exception is that the ring atom at the C10 position must be carbon.

Thus, in one aspect, one of the ring carbon atoms is replaced with nitrogen and representative compounds of formula I have the following structures:

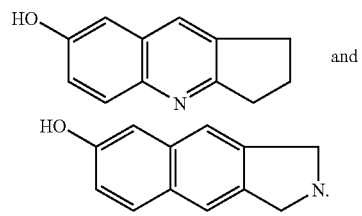

In another aspect, two of the ring carbon atoms are replaced with nitrogen and a representative compound of formula I may have the following structure:

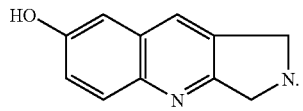

In yet another aspect, three of the ring carbon atoms may be replaced with nitrogen. In this regard, any three carbon atoms except the carbon atom at the C10 position may be replaced with nitrogen.

In formula I, only the ring atom at the C10 position is specifically shown to be substituted with a non-hydrogen substituent. However, as further noted above, formula I is defined herein to encompass compounds wherein any one or more of the A, B and C rings may be substituted with one or more optional non-hydrogen substituents. This feature of the compounds of formula I is shown by the designations $R^a$, $R^b$ and $R^c$, where $R^a$ represents one or more optional non-hydrogen substituents on the A ring, and $R^b$ and $R^c$ have analogous definitions for the B and C rings, respectively. Furthermore, formula I is defined herein to encompass compounds wherein two $R^a$ substituents, two $R^b$ substituents and/or two $R^c$ substituents, together with the ring atoms to which they are attached, may optionally be joined together to form a carbocyclic or heterocyclic ring. In various embodiments, $R^a$, $R^b$ and $R^c$ have, in total, no more than 30 carbon atoms and no more than 5 oxygen atoms.

Representative $R^a$, $R^b$ and $R^c$ groups include alkyl, substituted alkyl, alkenyl, substituted alkenyl, alkynyl, substituted alkynyl, alkoxy, substituted alkoxy, acyl, substituted acyl, aryl, substituted aryl, heteroalkyl, substituted heteroalkyl, heteroaryl, substituted heteroaryl, heterocycle, substituted heterocycle, formyl and halogen.

For example, in one aspect of the present invention, no optional $R^a$ substituents are present, i.e., the A ring has no substitutions beyond the hydroxy group at the C10 position. In another aspect, $R^b$ represents an alkyl group at the C7 position as the only optional substituent on the B ring. In yet another aspect, $R^c$ represents two optional substituents on the C ring which are joined together, in particular, $R^c$ represents the well-known D and E rings of SN-38, i.e., the compound of formula I is substituted with D and E rings as shown below:

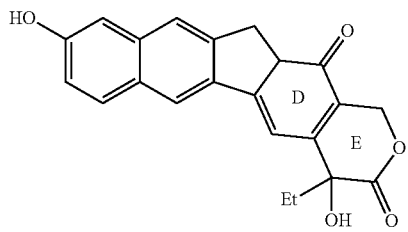

Accordingly, in one aspect of the present invention, the starting material used in the process of the present invention has the formula II, as follows:

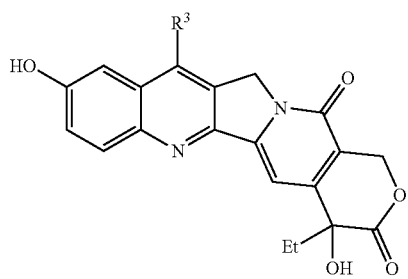

wherein $R^3$ is hydrogen or an alkyl group, and each of the ring atoms is carbon or nitrogen as shown. In one aspect, $R^3$ is ethyl. In another aspect, $R^3$ is hydrogen. In another aspect, $R^3$ is a $C_1$-$C_6$ alkyl group. The compounds of formula II are particularly similar to SN-38, and thus are a typical starting material. However, the process of the present invention is more generally applicable to compounds of formula I.

Amine of Formula $R^1R^2NH$

A second reactant in the process of the present invention is an amine of the formula $R^1R^2NH$. As for groups $R^1$ and $R^2$, these represent organic groups, where in various embodiments of the invention, $R^1$ and $R^2$ have, in total, less than 20 non-hydrogen atoms, or less than 15 non-hydrogen atoms.

Representative $R^1$ and $R^2$ groups include alkyl, substituted alkyl, alkenyl, substituted alkenyl, alkynyl, substituted alkynyl, alkoxy, substituted alkoxy, acyl, substituted acyl, aryl, substituted aryl, heteroalkyl, substituted heteroalkyl, heteroaryl, substituted heteroaryl, heterocycle and substituted heterocycle.

The $R^1$ and $R^2$ groups may be separate from one another, e.g., as in the structures:

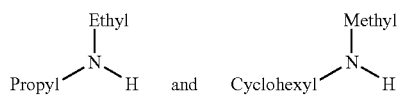

or the $R^1$ and $R^2$ groups may be joined together, e.g., as in the structures:

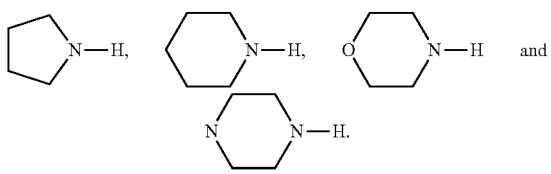

When the $R^1$ and $R^2$ groups are joined together, the heterocyclic ring that is thereby formed may optionally be substituted, e.g., as in the structures:

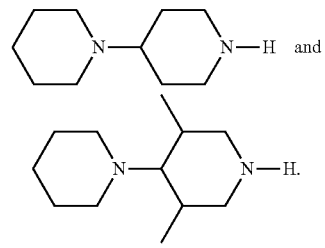

An amine of the structure

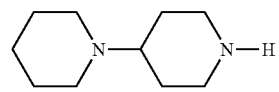 [SMILES: C1CCN(C2CCNCC2)CC1]

is a typical compound of formula $R^1R^2NH$ according to the present invention because this amine duplicates the sidechain present in irinotecan.

Phosgene or a Reactive Equivalent Thereof

In addition to the compounds of formula I and amines of the formula $R^1R^2NH$, the third reactant that is employed in the process of the invention is phosgene or a reactive equivalent thereof. Examples of reactive equivalents of phosgene include phosgene dimer (also known as trichloromethyl chloroformate or diphosgene), phosgene trimer (also known as triphosgene or bistrichloromethyl carbonate), carbonyldiimidazole and a combination of di-tert-butyl carbonate (DIBOC) with 4-(N,N-dimethylamino)pyridine (DMAP). Phosgene and the reactive equivalents thereof may be in solid (e.g., phosgene trihydrate), liquid or gaseous form.

In the method of the present invention, a compound of formula I, a compound of formula $R^1R^2NH$, and phosgene or a reactive equivalent thereof are reacted. These three reactants are combined in a single reaction vessel. The order of addition is not critical. In one aspect, the phosgene compound is added to the vessel, followed by addition of the $R^1R^2NH$ compound, followed by addition of the formula I compound. However, other orders of combination may also be employed.

A solvent will also typically be present in the reaction vessel. Exemplary solvents include halogenated solvents (e.g., dichloromethane and chloroform), ethereal solvents (e.g., diethyl ether and tetrahydrofuran), and glymes.

In addition to the solvent, a base is also typically present. The base is thought to act by activating the hydroxy group at the C10 position of the compound of formula I so that it is more reactive and will convert to the desired sidechain moiety. In one aspect, the base is a nitrogen-containing compound, e.g., pyridine, DABCO, tertiary amines and the like. A catalytic amount of a condensing agent can also be added, such as DMAP or DCC and the like.

The reaction temperature is typically between about −25° C. and +25° C., however other temperatures may be employed. The temperature primarily affects the rate of reaction, and may be adjusted to achieve a reaction rate that is convenient for the operator.

After the reactants are combined, they are left in combination for a sufficient time to form the side chain at C10. This time is typically on the order of 30 minutes to 5 hours when the reaction temperature is held between −10 and 0° C. The reaction may be conducted under an inert atmosphere, e.g., nitrogen or argon. The reaction vessel contents are typically stirred or otherwise agitated.

In one aspect of the invention, the compound of formula I and the amine of formula $R^1R^2NH$ are, respectively, SN-38, having the following structure:

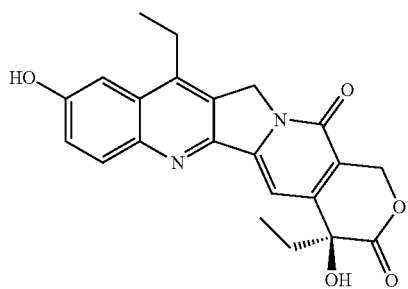 [SMILES: CCc1c2c(nc3ccc(O)cc13)-c1cc3c(c(=O)n1C2)COC(=O)[C@]3(O)CC]

piperidinopiperidine, having the structure:

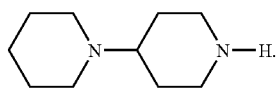

In the foregoing embodiment, when the compound of formula I is SN-38, and the amine of formula $R^1R^2NH$ is piperidinopiperidine, a compound of formula III is formed, namely, irinotecan, having the following structure III-A:

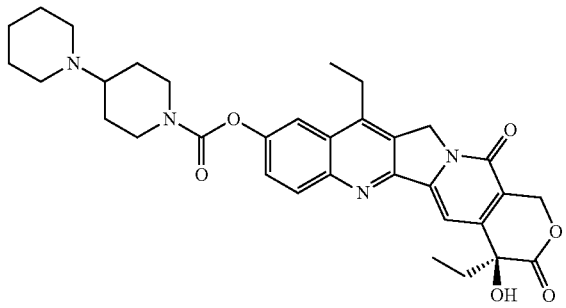 [SMILES: CCc1c2c(nc3ccc(OC(=O)N4CCC(N5CCCCC5)CC4)cc13)-c1cc3c(c(=O)n1C2)COC(=O)[C@]3(O)CC]

The product mixture obtained by combining a compound of formula I, a compound of formula $R^1R^2NH$, and phosgene or reactive equivalent thereof may be subjected to a purification scheme to obtain a compound of formula III in relatively pure form. For example, the product mixture may be filtered and the supernatant subjected to a solvent removal process (e.g., rotary evaporation). The residue may then be further purified by column chromatography, precipitation or crystallization. For example, the residue may be dissolved in a solvent, e.g., dichloromethane, and applied to a silica gel column. Elution with a gradient or mixture of dichloromethane and methanol affords a purified compound of formula III.

The process of the present invention wherein a sidechain is added to a compound of formula I is very efficient. This one-pot procedure may yield a final product of formula III in greater than 50% molar yield, based on the moles of compound of formula I employed. In further aspects, the molar yield is greater than 75% based on the moles of compound of formula I used in the process. In yet further aspects, the molar yield is greater than 90% based on the moles of compound of formula I used in the process. In a specific embodiment, the molar yield is 94% based on the moles of compound of formula I used in the process.

In those instances where the product is a basic, nitrogen-containing compound, then a further embodiment of the present invention provides a purification process for the product wherein the product is converted into a salt form. Such a purification process includes combining a product mixture comprising a nitrogen-containing compound (e.g., irinotecan) with a chlorinated solvent (e.g., dichloromethane (DCM)) or an aqueous solvent (e.g., water) and cooling this mixture to about 0° C. This solution is then acidified by adding an acid (e.g., 12N HCl) drop wise with stirring over a period of 2-3 hours. The solvent is evaporated to leave a solid residue which is dissolved in an alcoholic solvent (e.g., ethanol or methanol) and precipitated by addition of an ether solvent (e.g., diethyl ether). The precipitate is washed with the ether solvent to afford the pure salt.

The present invention is further illustrated by the following non-limiting examples. Unless otherwise noted, all scientific and technical terms have the meanings as understood by one of ordinary skill in the art.

EXAMPLES

Example 1

Phosgene trihydrate was dissolved in a chlorinated solvent, such as DCM under an argon atmosphere and cooled down to a low temperature in the range of −10 to 0° C. To this solution was added sequentially, piperidinopiperidine in DCM drop wise, followed by the addition of N,N-diisopropylethylamine (Hünig's base) or TEA drop wise. The reaction mixture was stirred at this temperature for one hour and slowly warmed to around room temperature and kept at this temperature for 2 hours.

After this time, a solution of SN-38 in pyridine was added drop wise and the solution was left to react for 30 minutes to 2 hours or until the complete consumption of starting material as evidenced by TLC.

The reaction was filtered and concentrated under vacuum to get the crude product. The crude product was dissolved in DCM and washed with water, dried over anhydrous $Na_2SO_4$ or $MgSO_4$ and evaporated. This material was purified either by column chromatography using silica gel and eluted with mixture of DCM/MeOH or precipitation or crystallization to obtain the pure product, namely, irinotecan (i.e., the compound of formula III-A). The yield of the desired product is 94%.

Example 2

The product from Example 1 was dissolved in DCM and cooled down to 0° C. 12N HCl was added drop wise to this solution and stirred for 2-3 hours. The solvent was evaporated to get a solid which was dissolved in methanol and precipitated by addition of diethyl ether. The precipitate is washed by ether 3 times to afford the pure product, namely, the salt form of irinotecan (i.e., the compound of formula III-A). The yield of the desired product is quantitative.

Alternatively, the product from Example 1 is dissolved in water and 12N HCl is added drop wise to the solution. The product precipitates out and is obtained by filtration. The yield is 95%.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A process for adding a side chain to a starting material comprising reacting together in a one-pot reaction:

(i) a compound of formula I:

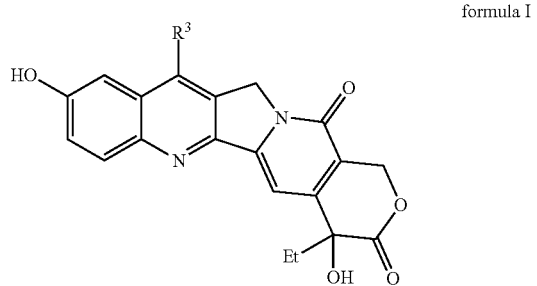

formula I or a partially or completely purified stereoisomer thereof, or a salt thereof, wherein $R^3$ is an alkyl group;

(ii) an amine of formula $R^1R^2NH$ wherein $R^1$ and $R^2$ are the same or different and independently represent organic groups having, in total, less than 20 non-hydrogen atoms and include alkyls, substituted alkyls, alkenyls, substituted alkenyls, alkynyls, substituted alkynyls, alkoxys, substituted alkoxys, acyls, substituted acyls, aryls, substituted aryls, heteroalkyls, substituted heteroalkyls, heteroaryls, substituted heteroaryls, heterocycles and substituted heterocycles; and (iii) phosgene or a reactive equivalent thereof, to provide a solution comprising a compound of formula III:

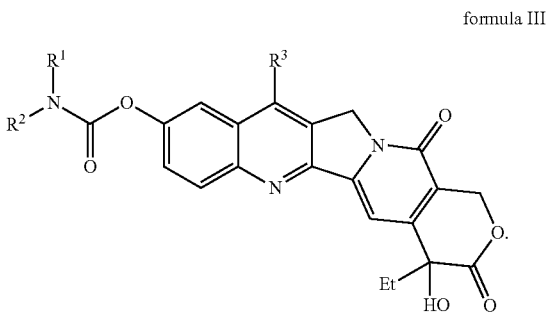

formula III

2. The process of claim 1 wherein the amine of formula $R^1R^2NH$ is piperidinopiperidine.

3. The process of claim 1 wherein the phosgene or a reactive equivalent thereof is phosgene trihydrate.

4. The process of claim 1 wherein the phosgene or reactive equivalent thereof and the amine of formula $R^1R^2NH$ are combined to provide an intermediate solution, and the compound of formula I is added to the intermediate solution.

5. The process of claim 4 further comprising adding pyridine or a tertiary amine to the intermediate solution along with the compound of formula I.

6. The process of claim 1 further comprising a step wherein the solution comprising a compound of formula III is filtered and then freed from solvent to provide a residue.

7. The process of claim 6 wherein the residue is purified by column chromatography, filtration, precipitation or crystallization.

8. The process of claim 1 wherein the molar yield of the compound of formula III is at least 50% based on the moles of the compound of formula I used in the process.

9. The process of claim 1 wherein the molar yield of the compound of formula III is at least 75% based on the moles of the compound of formula I used in the process.

10. The process of claim 1 wherein the molar yield of the compound of formula III is at least 90% based on the moles of the compound of formula I used in the process.

11. The process of claim 1 wherein the molar yield of the compound of formula III is 94% based on the moles of the compound of formula I used in the process.

12. The process of claim 1 wherein the compound of formula I is SN-38, the amine of formula $R^1R^2NH$ is piperidinopiperidine, and the compound of formula III is irinotecan, and wherein the process is a one-pot operation.

13. The process of claim 12 wherein the phosgene or reactive equivalent thereof is phosgene trihydrate, and the phosgene trihydrate and piperidinopiperidine are combined in a solvent and allowed to react together to form an intermediate solution, and the SN-38 and an organic base are added to the intermediate solution to form the solution comprising irinotecan.

14. The process of claim 13 wherein the phosgene trihydrate is dissolved in a chlorinated solvent and then cooled to a temperature in the range of −40° C. to 25° C. followed by addition of piperidinopiperidine to the cooled solution.

15. The process of claim 14 wherein the phosgene trihydrate is cooled to a temperature in the range of −10° C. to 0° C.

16. The process of claim 14 wherein, subsequent to the addition of piperidinopiperidine, N,N-diisopropylethylamine, triethylamine or an equivalent base is added to the cooled solution.

17. The process of claim 16 further comprising adding a catalyst to the intermediate solution along with the SN-38 and the organic base.

18. The process of claim 17 wherein the organic base is pyridine or the like.

19. The process of claim 17 wherein the catalyst is DMAP, DCC or the like.

* * * * *